United States Patent
Daub

[11] 3,930,312
[45] Jan. 6, 1976

[54] DENTAL ARTICULATOR

[76] Inventor: Hans Daub, Gustav-von-Mevissen-Str. 72, 59 Siegen, Germany

[22] Filed: Jan. 17, 1974

[21] Appl. No.: 434,205

[30] Foreign Application Priority Data
Jan. 17, 1973   Germany............................ 2302086

[52] U.S. Cl. .................................................. 32/32
[51] Int. Cl.² ...................................... A61C 11/00
[58] Field of Search ........................................ 32/32

[56] References Cited
UNITED STATES PATENTS

| | | | |
|---|---|---|---|
| 683,640 | 10/1901 | Cross ...................................... | 32/32 |
| 2,029,003 | 1/1936 | Spiro ...................................... | 32/32 |
| 2,697,279 | 12/1954 | Clawson ................................... | 32/32 |
| 2,731,723 | 1/1956 | Brandhandler ........................... | 32/32 |
| 2,786,272 | 3/1957 | Lindleg ................................... | 32/32 |

FOREIGN PATENTS OR APPLICATIONS

148,991   3/1904   Germany

*Primary Examiner*—Robert Peshock
*Attorney, Agent, or Firm*—Young & Thompson

[57] ABSTRACT

A dental articulator comprises a pair of upper and lower brackets for upper and lower artificial dentures, respectively, with a support between the two brackets. The upper bracket is pivotally interconnected to the support for vertical swinging movement of the upper bracket relative to the occlusal plane of the articulator. The support and the lower bracket are slidably interconnected for relative movement in a forward and rearward direction parallel to the occlusal plane and perpendicular to the axis of vertical swinging of the upper bracket. The support and lower bracket can also have limited relative rotational movement in a plane parallel to the occlusal plane. A plate is insertable and removable in the articulator in inverted positions, so that in one position the upper surface of the plate lies in the occlusal plane and in the inverted position the under surface of the plate lies in the occlusal plane.

2 Claims, 5 Drawing Figures

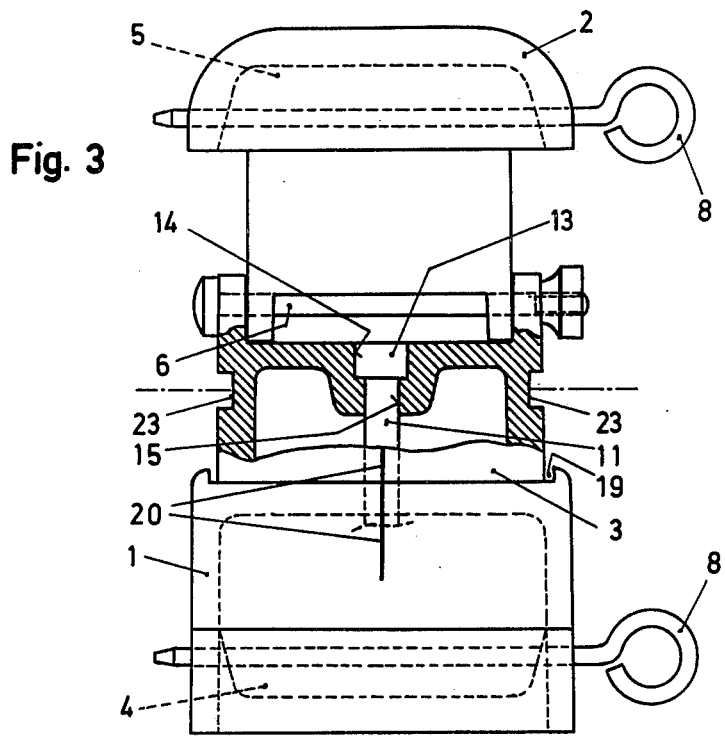
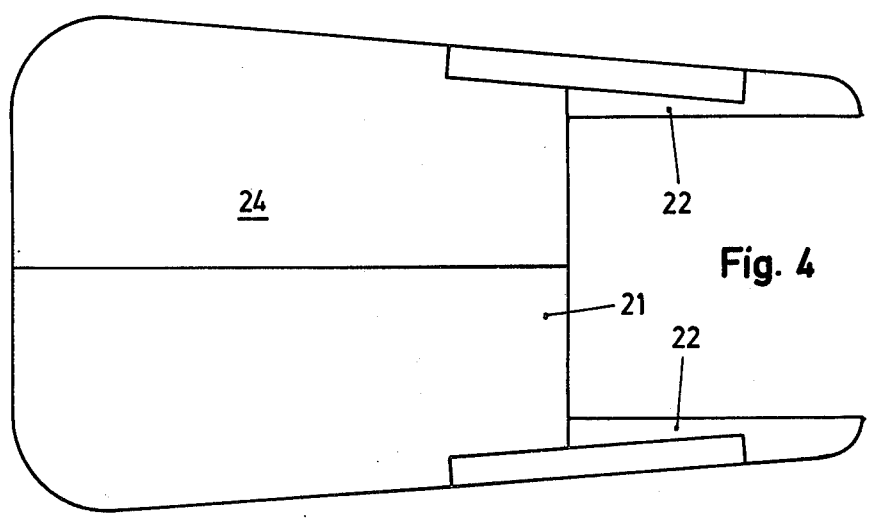
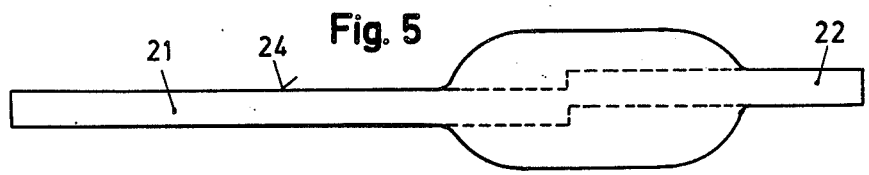

DENTAL ARTICULATOR

The present invention relates to dental articulators for the functionally proper positioning of the teeth for upper and lower artificial dentures, with a lower bracket and an upper bracket for the attachment of the artificial dentures by means of plaster of Paris or the like, wherein the upper bracket, fastened to a support, is movably mounted with respect to the lower bracket, and the support of the upper bracket is rotatable with respect to a receiving element in a plane in parallel to the occlusal plane and is mounted to be linearly reciprocably displaceable toward the rear from a forward stop or abutment.

Such a dental articulator is disclosed in German Patent No. 1,616,465. The upper and lower brackets are formed from wires fastened within the supports. These wires have a certain inherent resiliency, which is undesirable for the proper positioning of the artificial dentures, even though the resultant minor misalignments can be equalized later on in the mouth.

It is accordingly an object of this invention to provide an improved and particularly a more stable or sturdy construction for such a dental articulator.

This object is achieved, in accordance with the present invention, by constructing the brackets for the mounting of the artificial denture to be dish-shaped and integral with their respective supports to form an upper part and a lower part of the articulator. The joint corresponding to the hinge of the jaws, that is, the temporomaxillary articulation, is a hinge between the upper part and the receiving element. The upper and lower parts preferably have each a dish-like indentation for receiving the plaster of Paris or other hardenable mounting material. In the wall portions defining the dish-like indentation, holes aligned in pairs can be provided for the reception of a locking pin.

Another advantageous feature of the invention is that the topside of the upper part extends obliquely downwardly in the rearward direction, and the underside of the lower part extends obliquely upwardly in the rearward direction. The lower part and the receiving element are advantageously connected with each other by means of a screw having a knurled nut and a compression spring. The screw, the head of which is fixed in a recess of the receiving element, extends through a slotted hole in the lower part, which slotted hole limits the linear reciprocating motion of the upper part relative to the lower part. The compression spring is housed in a spring cage between the knurled nut and a shim or supporting disk contacting the lower part, and the spring cage can be pressed by the knurled nut against the shim in order to fix the upper and lower parts in position.

As another feature of the invention, the receiving element is guided on the lower part with lateral play permitting a limited horizontal pivotal motion of the receiving element and thus also of the upper part relative to the lower part about the screw. The receiving element and the lower part can be provided with a marking which indicates the neutral central position. Furthermore, a plate can be provided which defines the occlusal plane with one of its surfaces. This plate can be inserted, with bifurcated members, in lateral guide grooves of the receiving element, wherein the surface of the plate representing the occlusal plane lies in the common plane of symmetry of the bifurcated members. Thereby, the plate can also be inserted in the reverse position, so that the dental prosthesis can be made to approach the occlusal plane from the top as well as from the bottom.

Other objects, features and advantages of the present invention will become apparent from a consideration of the following description, when in connection with the accompanying drawings, in which:

FIG. 3 is a view from the left of the articulator of FIGS. 1 and 2;

FIG. 4 is a top plan view of the plate defining the occlusal plane; and

FIG. 5 is a side elevational view of the plate of FIG. 4.

Figure 1:
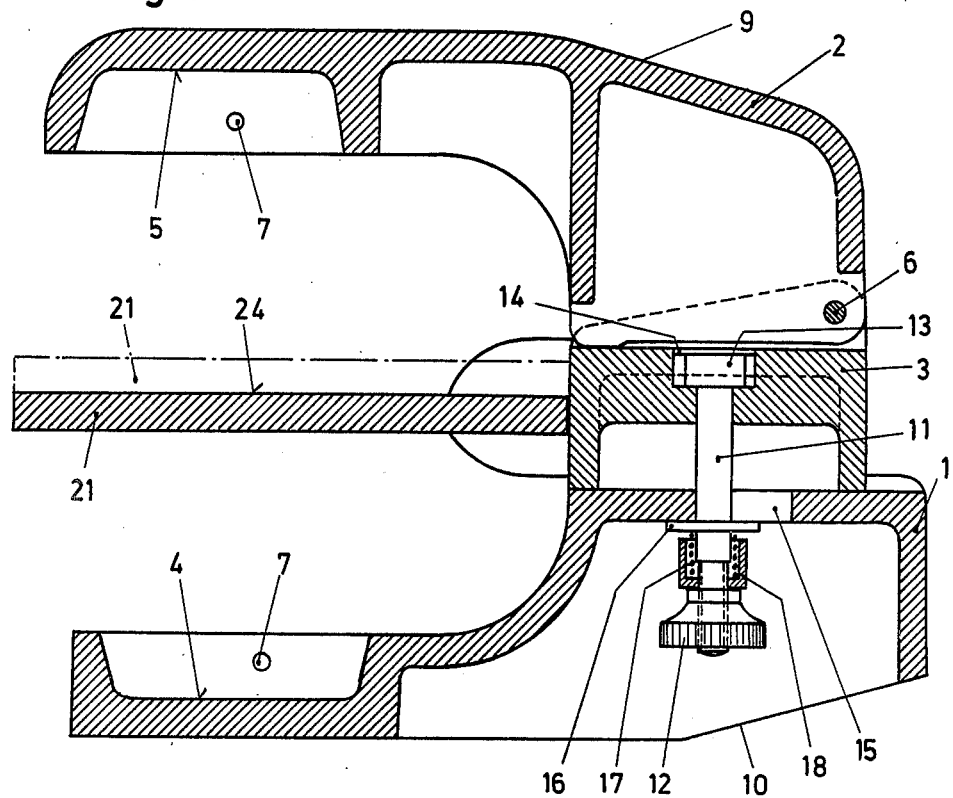
FIG. 1 is a vertical cross-sectional view of a dental articulator according to the present invention.

Referring now to the drawings in greater detail, the dental articulator illustrated therein comprises an integrally formed lower part 1 and an integrally formed upper part 2, between which a receiving element 3 is arranged. The lower and upper parts 1, 2 each have a dish-like indentation 4 and 5, respectively, to receive the plaster of Paris or other hardenable material for the mounting of the respective dental prosthesis (not shown). A hinge 6 is provided between the upper part 2 and the receiving element 3, so that the upper part can be flipped upwardly. In the wall portions defining the dish-like indentations 4, 5 holes 7 aligned in pairs are disposed to receive each one locking pin 8.

The topside of the upper part 2 extends obliquely downwardly in the rearward direction, as seen at 9 in FIG. 1 and and the underside of the lower part 1 extends obliquely upwardly at 10. This affords the advantage that, with the upper part 2 flipped upwardly, the articulator can be placed on either one of the inclined surfaces 9 and 10, so that the adjusted dentures can be observed in the direction of the occlusal plane without having to change one's own body position in any particular way.

The lower part 1 and the receiving element 3 are joined by a screw 11 with a knurled nut 12. The head 13 of the screw 11 is non-circular and is disposed in a correspondingly shaped recess 14 of the receiving element 3, forming a support for the upper part 2, so that screw 11 and element 3 cannot rotate relative to each other. The screw 11 extends downwardly through a slotted hole 15 which limits the linear reciprocating movement of the receiving element 3 and thus of the upper part 2 with respect to the lower part 1.

Figure 2:
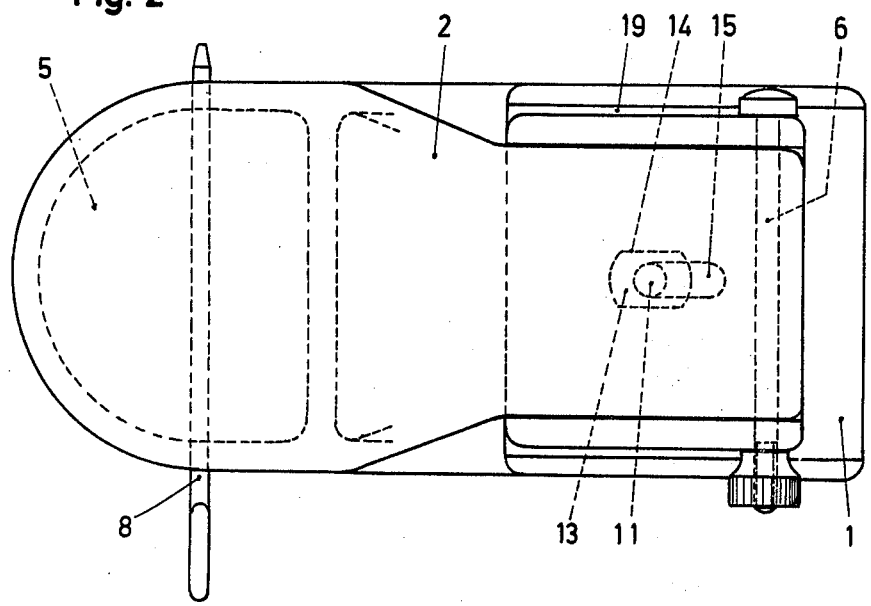
FIG. 2 is a top plan view thereof.

A compression spring 17 is clamped between the knurled nut 12 and shim 16 contacting the lower part 1. This compression spring is surrounded by a spring cage 18 (FIG. 1). When the knurled nut 12 is slightly slackened, the receiving element 3 with the upper part 2 can be displaced frictionally on the lower part 1. Since the receiving element 3, as shown in FIGS. 2 and 3, is guided on the bottom part 1 with a lateral play 19, it is also possible to execute a limited rotary movement of element 3 about and with the screw 11. In order to mark the neutral central position, the receiving element 3 and the lower part 1 have a marking 20 (FIG. 3). By tightening the knurled nut 12 by way of the spring cage 18, the lower and upper parts 1, 2 can be fixed with respect to each other in any desired position within the limits provided by the slotted hole 15 and the clearance 19.

In order to fix the occlusal plane, a plate 21 is provided (FIGS. 1, 4 and 5), which can be inserted with bifurcated members 22 in lateral guide grooves 23 (FIG. 3) of the receiving element 3. The plate 21 is illustrated in detail in FIGS. 4 and 5. The surface 24, representing the occlusal plane, lies exactly in the horizontal and/or common central plane of the bifurcated members 22, as shown in FIG. 5, so that the plate 21, as shown in FIG. 1 in dot-dash lines, can also be inserted in an inverted position and thus the occlusal plane is accessible from above or from below.

From a consideration of the foregoing disclosure, therefore, it will be evident that all of the initially recited objects of the present invention have been achieved.

Although the present invention has been described and illustrated in connection with a preferred embodiment, it is to be understood that modifications and variations may be resorted to without departing from the spirit of the invention, as those skilled in this art will readily understand. Such modifications and variations are considered to be within the purview and scope of the present invention as defined by the appended claims.

Having described my invention, I claim:

1. A dental articulator for properly positioning upper and lower artificial dentures relative to each other and relative to an intermediate occlusal plane which is the bite plane when artificial dentures are mounted on the articulator, comprising an upper bracket and a lower bracket for the detachable securement thereto of said upper and lower dentures, respectively, a support on which said upper bracket is pivotally mounted for swinging movement about an axis parallel to said occlusal plane, means adjustably interconnecting said support and said lower bracket for movement of said support and said lower bracket relative to each other in a direction perpendicular to said axis and parallel to said occlusal plane, a plate carried by and extending forwardly from said support and disposed between said upper and lower bracket, said plate having one surface thereof confronting one of said brackets and disposed in said occlusal plane, and means mounting said plate so that when said plate is disposed in one position on said articulator the upper surface of said plate lies in said occlusal plane and when said plate is inverted and disposed in an inverted position in said articulator the undersurface of said plate is disposed in said occlusal plane whereby said occlusal plane may be established relative to an upper set of artificial dentures in said one position of said plate and said occlusal plane may be established relative to a lower set of artificial dentures in said inverted position of said plate.

2. A dental articulator as claimed in claim 1, said mounting means comprising bifurcated members carried by said plate and releasably received in lateral guide grooves of said support.

* * * * *